(12) United States Patent
Pol et al.

(10) Patent No.: US 9,748,572 B2
(45) Date of Patent: Aug. 29, 2017

(54) ULTRASOUND ASSISTED IN-SITU FORMATION OF CARBON/SULFUR CATHODES

(71) Applicant: UChicago Argonne, LLC, Chicago, IL (US)

(72) Inventors: Vilas G. Pol, Naperville, IL (US); Wei Weng, Woodridge, IL (US); Khalil Amine, Oak Brook, IL (US)

(73) Assignee: UCHICAGO ARGONNE, LLC, Chicago, IL (US)

( * ) Notice: Subject to any disclaimer, the term of this patent is extended or adjusted under 35 U.S.C. 154(b) by 936 days.

(21) Appl. No.: 13/790,521

(22) Filed: Mar. 8, 2013

(65) Prior Publication Data
US 2013/0337347 A1 Dec. 19, 2013

Related U.S. Application Data

(60) Provisional application No. 61/660,917, filed on Jun. 18, 2012.

(51) Int. Cl.
H01M 4/58 (2010.01)
H01M 4/583 (2010.01)
H01M 4/139 (2010.01)
H01M 4/1393 (2010.01)
H01M 4/1397 (2010.01)
C07C 319/14 (2006.01)
(Continued)

(52) U.S. Cl.
CPC ........... *H01M 4/583* (2013.01); *C07C 319/14* (2013.01); *H01M 4/364* (2013.01); *H01M 4/38* (2013.01); *H01M 4/5815* (2013.01); *H01M 4/625* (2013.01); *H01M 10/052* (2013.01); *H01M 10/0569* (2013.01)

(58) Field of Classification Search
CPC ........ H01M 4/04–4/0497; H01M 4/13; H01M 4/133; H01M 4/136; H01M 4/139–4/1399
See application file for complete search history.

(56) References Cited

U.S. PATENT DOCUMENTS 3,898,098 A * 8/1975 Giles ............... H01M 4/52
205/66
6,194,099 B1 * 2/2001 Gernov ............ H01M 4/36
29/623.5
(Continued)

FOREIGN PATENT DOCUMENTS

JP WO 2010035602 A1 * 4/2010 ............ H01M 4/581

OTHER PUBLICATIONS

Cao et al. (2011) Sandwich-type functionalized graphene sheet-sulfur nanocomposite for rechargeable lithium batteries. Phys. Chem. Chem. Phys., 2011 (13), 7660-7665. doi: 10.1039/C0CP02477E (Mar. 30, 2011).*

(Continued)

Primary Examiner — Jonathan Crepeau
Assistant Examiner — Jacob Buchanan
(74) Attorney, Agent, or Firm — Foley & Lardner LLP

(57) ABSTRACT

A process of preparing an E-carbon nanocomposite includes contacting a porous carbon substrate with an E-containing material to form a mixture; and sonicating the mixture to form the E-carbon nanocomposite; where E is S, Se, $Se_xS_y$, or Te, x is greater than 0; and y is greater than 0.

12 Claims, 15 Drawing Sheets

(51) Int. Cl.
*H01M 4/36* (2006.01)
*H01M 4/38* (2006.01)
*H01M 4/62* (2006.01)
*H01M 10/052* (2010.01)
*H01M 10/0569* (2010.01)

(56) References Cited

U.S. PATENT DOCUMENTS

| | | | |
|---|---|---|---|
| 7,019,494 B2 | 3/2006 | Mikhaylik | |
| 7,066,971 B1 | 6/2006 | Carlson | |
| 2003/0143464 A1* | 7/2003 | Yamamoto | B82Y 30/00 429/231.95 |
| 2011/0165466 A1 | 7/2011 | Zhamu et al. | |
| 2011/0171537 A1* | 7/2011 | Takeuchi | C01B 17/22 429/322 |
| 2011/0200883 A1* | 8/2011 | Cui | H01M 4/049 429/231.4 |
| 2011/0206992 A1* | 8/2011 | Campbell | H01M 4/80 429/235 |
| 2013/0164626 A1* | 6/2013 | Manthiram | B82Y 30/00 429/231.8 |

OTHER PUBLICATIONS

Ji et al. (2011) Porous carbon nanofiber-sulfur composite electrodes for lithium/sulfur cells. Energy Environ. Sci., 2011 (4), 5053-5059. doi: 10.1039/C1EE02256C (Oct. 18, 2011).*

Yin et al. (2011) A novel pyrolyzed polyacrylonitrile-sulfur@MWCNT composite cathode material for high-rate rechargeable lithium/sulfur batteries. J. Mater. Chem., 2011, (21), 6087-6810. Doi: 10.1039/c1jm00047k (Apr. 8, 2011).*

Ji et al. (2009) A highly ordered nanostructured carbon-sulphur cathode for lithium-sulphur batteries. Nature Materials, 2009 (8), 500-506. doi: 10.1038/nmat2460 (May 17, 2009).*

Fu et al. (2012) Sulfur-Carbon Nanocomposite Cathodes Improved by an Amphiphilic Block Copolymer for High-Rate Lithium-Sulfur Batteries. ACS Applied Materials & Interfaces 2012 4 (11), 6046-6052 DOI: 10.1021/am301688h.*

Guo, J., et al. "Sulfur-Impregnated Disordered Carbon Nanotubes Cathode for Lithium-Sulfur Batteries," Nano Lett. 2011, vol. 11, pp. 4288-4294.

Ji, et al., "A highly ordered nanostructured carbon-sulphur cathode for lithium-sulphur batteries", Nature Materials, vol. 8, Jun. 2009, 500-506.

Li, K., et al., "Enhance electrochemical performance of lithium sulfur battery through a solution-based processing technique," Journal of Power Sources 202, 2012, pp. 389-393.

McNamara III, W., et al., "Sonoluminescence Temperatures During Multibubble Cavitation" Nature, 1999, 401, pp. 772-775.

Wang, H., et al., "Graphene-Wrapped Sulfur Particles as a Rechargeable Lithium-Sulfur Battery Cathode Material with High Capacity and Cycling Stability," Nano Lett., 2011, vol. 11, pp. 2644-2647.

Zyga, L., "Rechargeable lithium-sulfur batteries get a boost from graphene." Phys.org. Jul. 13, 2011, retrieved from: http://phys.org/news/2011-07-rechargeable-lithium-sulfur-batteries-boost-graphene.html, 3 pages.

* cited by examiner

FIG. 3A (upper) and 3B (lower)

ULTRASOUND ASSISTED IN-SITU FORMATION OF CARBON/SULFUR CATHODES

CROSS-REFERENCE TO RELATED APPLICATIONS

This U.S. patent application claims the benefit of U.S. Provisional Patent Application No. 61/660,917, filed Jun. 18, 2012, the entire content of which is incorporated herein by reference in its entirety for any and all purposes.

GOVERNMENT RIGHTS

The United States Government has rights in this invention pursuant to Contract No. DE-AC02-06CH11357 between the United States Government and UChicago Argonne, LLC, representing Argonne National Laboratory.

FIELD

The present technology is generally related to carbon materials for electrochemical cells.

BACKGROUND

The emerging electric vehicle and plug-in hybrid vehicle technologies mandate significant improvement of rechargeable battery technologies to achieve higher energy density. Despite the plentiful advantages, the overall energy density of lithium-ion batteries is limited by the low capacity of present cathode materials. Therefore, rechargeable batteries beyond lithium-ion have been widely investigated as alternatives. Among them, the lithium-sulfur battery (Li-SB) is an attractive technology for a number of reasons. For example, Li-SBs have a theoretical capacity of 1675 mAh and a very high specific energy density of about 2500 Wh kg-I, they are made with non-poisonous and abundant sulfur, and the LiSBs exhibit an intrinsic protection mechanism from overcharge due to soluble polysulfides, thereby providing an inherent measure of safety.

Despite the great promises, there still are a number of complex problems need to be solved for the commercialization of Li-SBs. Such problems include the formation of electrically insulating lithium polysulfides ($Li_2S_n$) which can diffuse to the anode and directly react with Li metal to form lower order polysulfides including insoluble $Li_2S_2$ and $Li_2S$, which will deposit on the Li anode. The lower order polysufides can also diffuse back to the cathode where they are oxidized to higher order polysulfides, thus forming an undesirable shuttle mechanism. Finally, Li-SBs tend to exhibit a rapid decrease in capacity during cycling, as well as high self-discharge rates.

SUMMARY

In one aspect, a process of preparing an E-carbon nanocomposite is provided. The process includes contacting a porous carbon substrate with an E-containing material to form a mixture; and sonicating the mixture to form the E-carbon nanocomposite, where E is S, Se, $Se_xS_y$, or Te, x is greater than 0, and y is greater than 0. In one embodiment, the E-containing material may be a salt. In such embodiments, the salt and the porous carbon substrate may be contacted in an aqueous medium. In some embodiments, the aqueous medium may further include an acid. In any of the above embodiments, the sonicating may be performed at a frequency from about 20 Hz to about 100 Hz. In any of the above embodiments, the S, Se, $Se_xS_y$, or Te in the E-carbon nanocomposite is present from about 20 wt % to about 80 wt %. In any of the above embodiments, the porous carbon substrate may include microporous carbon, mesoporous carbon, mesoporous microbeads, graphite, expandable graphite, graphene, carbon black, or carbon nanotubes.

In another aspect, a process of preparing a $Li_2S$-carbon nanocomposite is provided. The process includes contacting a porous carbon substrate with a material containing lithium and sulfur in a solid state to form a mixture; heating the mixture to form a heated mixture; and sonicating the heated mixture to form the $Li_2S$-carbon nanocomposite. In some embodiments, the contacting and sonicating are performed under an inert atmosphere, or in a reducing atmosphere comprising an inert gas and hydrogen. In some embodiments, the material containing lithium and sulfur is a salt that includes both lithium and sulfur. According to various embodiments, the material containing lithium and sulfur includes $Li_2SO_4$ and $Li_2SO_3$. In any of the above embodiments, the sonicating may be performed at a frequency from about 20 Hz to about 100 Hz. In any of the above embodiments, the sulfur in the $Li_2S$-carbon nanocomposite is present from about 20 wt % to about 80 wt %. In any of the above embodiments, the porous carbon substrate may include microporous carbon, mesoporous carbon, mesoporous microbeads, graphite, expandable graphite, graphene, carbon black, or carbon nanotubes. In any of the above embodiments, the temperature is from about 600° C. to about 1000° C.

In another aspect, an electrochemical cell is provided including a cathode comprising a S-carbon nanocomposite, a Se-carbon nanocomposite, a Te-carbon nanocomposite, or a $Li_2S$-carbon nanocomposite; an anode; a separator; and an electrolyte. The S-carbon nanocomposite, Se-carbon nanocomposite, Te-carbon nanocomposite, or $Li_2S$-carbon nanocomposite may be any of those as are prepared by the above processes. In any of the above embodiments of the methods or the cells, porous carbon may be an electrically conductive, porous carbon having a pore diameter of less than about 100 nm, where the sulfur, selenium, tellurium, or $Li_2S$ are nanometer-sized particles deposited within the pores of the carbon or on the surface of the carbon. In any of the above embodiments, the anode may include lithium. In any of the above embodiments, the separator may be a polymer or ceramic separator.

The electrolyte may include a solvent and an alkali metal salt. In any of these embodiments, the solvent may include a fluorinated ether solvent, a siloxyl ether solvent, a silyl carbonate solvent, or a siloxyl carbonate solvent. In one embodiment, the solvent includes a fluorinated ether solvent.

DETAILED DESCRIPTION

Figure 1:
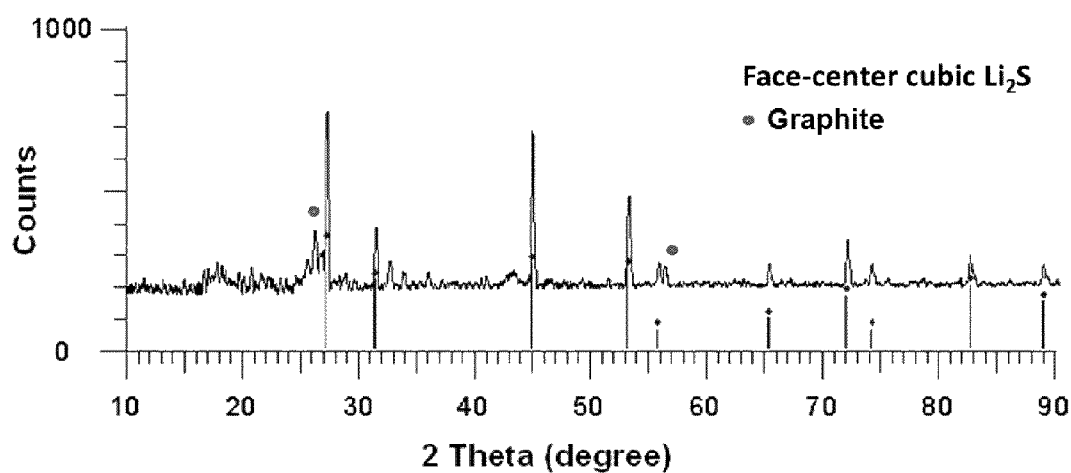
FIG. 1 is an XRD (x-ray diffraction) spectrum of a $Li_2S$-carbon nanocomposite prepared according to Example 1.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

In general, "substituted" refers to an alkyl, alkenyl, alkynyl, aryl, or ether group, as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

As used herein, "alkyl" groups include straight chain and branched alkyl groups having from 1 to about 20 carbon atoms, and typically from 1 to 12 carbons or, in some embodiments, from 1 to 8 carbon atoms. As employed herein, "alkyl groups" include cycloalkyl groups as defined below. Alkyl groups may be substituted or unsubstituted. Examples of straight chain alkyl groups include methyl, ethyl, n-propyl, n-butyl, n-pentyl, n-hexyl, n-heptyl, and n-octyl groups. Examples of branched alkyl groups include, but are not limited to, isopropyl, sec-butyl, t-butyl, neopentyl, and isopentyl groups. Representative substituted alkyl groups may be substituted one or more times with, for example, amino, thio, hydroxy, cyano, alkoxy, and/or halo groups such as F, Cl, Br, and I groups. As used herein the term haloalkyl is an alkyl group having one or more halo groups. In some embodiments, haloalkyl refers to a perhaloalkyl group.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 6, or 7. Cycloalkyl groups may be substituted or unsubstituted. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups may be mono-substituted or substituted more than once, such as, but not limited to: 2,2-; 2,3-; 2,4-; 2,5-; or 2,6-disubstituted cyclohexyl groups or mono-, di-, or tri-substituted norbornyl or cycloheptyl groups, which may be substituted with, for example, alkyl, alkoxy, amino, thio, hydroxy, cyano, and/or halo groups.

Alkenyl groups are straight chain, branched or cyclic alkyl groups having 2 to about 20 carbon atoms, and further including at least one double bond. In some embodiments alkenyl groups have from 1 to 12 carbons, or, typically, from 1 to 8 carbon atoms. Alkenyl groups may be substituted or unsubstituted. Alkenyl groups include, for instance, vinyl, propenyl, 2-butenyl, 3-butenyl, isobutenyl, cyclohexenyl, cyclopentenyl, cyclohexadienyl, butadienyl, pentadienyl, and hexadienyl groups among others. Alkenyl groups may be substituted similarly to alkyl groups. Divalent alkenyl groups, i.e., alkenyl groups with two points of attachment, include, but are not limited to, CH—CH=CH$_2$, C=CH$_2$, or C=CHCH$_3$.

As used herein, "aryl", or "aromatic," groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. The phrase "aryl groups" includes groups containing fused rings, such as fused aromatic-aliphatic ring systems (e.g., indanyl, tetrahydronaphthyl, and the like). Aryl groups may be substituted or unsubstituted.

Provided herein are processes of preparing carbon nanocomposites containing sulfur (S), selenium (Se), or tellurium (Te). Also provided are electrochemical cells containing the prepared nanocomposites, the prepared nanocomposites in conjunction with various electrolytes, and battery systems incorporating such nanocomposites. The processes include the use of ultrasonication of an E-containing material, where E is S, Se, Se$_x$S$_y$, or Te (x and y are greater than 0), in an aqueous medium to insert nanoparticle-sized, crystalline S, Se, Se$_x$S$_y$, or Te into a porous carbon substrate. The E-containing material may also be a solid solution of Se and S. Such solid solutions may be represented as Se$_x$S$_y$, where x and y are greater than 0. For example, x and y may individually be from 0.01 to 10.

The use of the sonication in the preparation of the nanocomposites provides a number of advantages over other processes for preparing an E-carbon composite. For example, it has been observed that the use of sonication-assisted reactions in the preparation of the nanocomposites provides for reduced reaction times and lower reaction temperatures in comparison to the reactions times without sonication. In previous methods of preparing sulfur-carbon composites, it was required to melt the sulfur before and/or during contact with the sulfur. The sonication avoids the excessive temperatures and conditions associated with the melting of S, Se, Se$_x$S$_y$, or Te. Sonication also allows for the use of crude, or technical grade reagents. Separately, the sonication activates the surfaces of substrates metals, modifying those surfaces, and enhancing the reactivity of the surfaces. The ultrasonic waves generated during sonication assist in oxidation and reduction reactions in the dissolution of solid reactants. Sonication achieves this by creating microscopic bubbles in a solution or melt, which upon collapse create a high-pressure environment from which microjets and shockwaves may emanate.

Accordingly, in one aspect, a process of preparing an E-carbon nanocomposite is provided, the process including contacting a porous carbon substrate with an E-containing material in an aqueous medium to form an aqueous mixture and sonicating the mixture to form the E-carbon nanocomposite. As noted above, E is S, Se, Se$_x$S$_y$, or Te. In one embodiment E is S. The process may also include an acid in the acid mixture to assist in reducing the S, Se, or Te and releasing it as a nano-E material for insertion in to the carbon. For example, where E is S, and the E-containing material is a thiosulfate S$_2$O$_3^{-2}$, the sulfur may be reduced in the presence of an acid such as HCl to produce S, SO$_2$ and water. Illustrative acids that may be used in the processes include, but are not limited to, HCl, HNO$_3$, H$_2$SO$_4$, H$_3$PO$_4$, HBr, and H$_2$S, or a mixture of any two or more acids. After formation of the E-carbon nanocomposite, the water is removed. The E-carbon material that is formed may include an integrated nano-structured network of nanometer-scale carbon filaments that are interconnected, forming a porous network of electron-conducting paths. The pores of the network have an average dimension of less than about 100 nm, with active S, Se, Se$_x$S$_y$, or Te confined within the pores. This structure avoids loss of the active S, Se, Se$_x$S$_y$, or Te, and reduces or eliminates the polysulfide shuttle reaction due to dissolution of the S, Se, Se$_x$S$_y$, or Te into the electrolyte.

The processes may also be performed under an inert atmosphere to prevent re-oxidation of the S, Se, Se$_x$S$_y$, or Te. The aqueous solution in which the sonication is performed may be deoxygenated by sparging or free-pump-thaw degassing in the presence of an inert gas. Illustrative inert gases include, but are not limited to, N$_2$, He, Ne, and Ar.

As described herein, sonication, identified in the reaction schemes as ")))))" in the same manner as a reaction arrow is used, can help promote the reaction of the E-containing materials. The E-containing materials may be a salt. By way of illustration only, the reaction of Na$_2$S$_2$O$_3$ with HCl, is assisted by sonication as set forth in Equations 1 and 2, below, where E is S.

H$_2$O))))))))H.+.OH  Eq. 1

Na$_2$S$_2$O$_3$+2HCl+H.+.OH)))))2NaCl+H$_2$O+S$^0$+SO$_2$  Eq. 2

The sulfur that is generated in Equation 2 is nanoparticulate in size. The sulfur that is formed may then be driven into a mesoporous carbon substrate, also using sonication, as set forth in Equation 3.

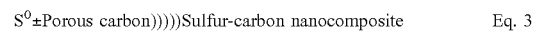

S$^0$±Porous carbon)))))Sulfur-carbon nanocomposite  Eq. 3

Analogous reactions may be used with other "E" materials and salts, other than NaS$_2$O$_3$, where the other "E" materials and salts contain an element that is S, Se, $Se_xS_y$, or Te. Illustrative "E" materials include, but are not limited to, $Na_2S_2O_3$, $Li_2S_2O_3$, $K_2S_2O_3$, and $(NH_4)_2S_2O_3$, hydrates of any such salts, or a mixture of any two or more such salts and/or hydrates of such salts. The "E" material may also be a solid solution of $Se_xS_y$, where x and y are greater than 0, and the material may be formed by a mixture of the elements or Se and S precursor materials as introduced above.

The sonicating of the aqueous mixture may be conducted at a frequency sufficient to effect the preparation of the sulfur from the sulfur containing salt and sufficient to drive the sulfur into the pores of the porous carbon substrate. For example, the sonicating may be performed at a frequency from about 20 Hz to about 100 Hz.

The porous carbon substrate into which the S, Se, $Se_xS_y$, or Te is inserted, may include high surface area carbon materials and/or nanoparticulate carbon materials. The porous carbon may have a pore diameter of less than about 100 nm, according to some embodiments. According to some other embodiments, the porous carbon may have a surface area of greater than 200 $m^2/g$. Such materials may include, but are not limited to, microporous carbon, mesoporous carbon, mesoporous microbeads, graphite, expandable graphite, graphene, carbon black, or carbon nanotubes. Commercial examples of carbon black include, but are not limited to, Super P, Black Pearl 2000, Denka Black, Vulcan XC72R, Ketjen black. As used herein, a mesoporous carbon substrate is a carbon substrate in which has a pore diameter from 2 nm to 50 nm. Usually, normal carbon substrates have less surface area and minimum pores. As used herein, a microporous carbon substrate is a carbon substrate in which has a pore diameter of less than 2 nm.

Through the process of using sonication to assist in the formation of a E-carbon nanocomposite, the surface area of the carbon changes upon addition of the S, Se, $Se_xS_y$, or Te. Because some of the surface area of the porous carbon material is attributable to the inside surface of the pores, as those pores are filled with S, Se, $Se_xS_y$, or Te, the surface area decreases. Additionally, the S, Se, $Se_xS_y$, or Te is uniformly distributed throughout the carbon. In some embodiments, the E-carbon nanocomposite has a surface area of less than 100 $m^2/g$. As illustrated below in the examples, experimental evidence is provided for the homogeneous inclusion of S throughout the carbon substrate. It is noted that this avoids agglomerations of S, Se, or Te in one area to the exclusion of the particular element from another area. The portions of the pores of the carbon are filled with the S, Se, $Se_xS_y$, or Te, or the S, Se, $Se_xS_y$, or Te is fully surrounded by the carbon thus sequestering the S, Se, $Se_xS_y$, or Te within the carbon and preventing, or minimizing the ability of the S, Se, $Se_xS_y$, or Te to migrate out of the carbon substrate. Sulfur has been used in the examples as illustrative of the group of S, Se, $Se_xS_y$, or Te.

It is noted that in the sulfur-carbon nanocomposites, thus prepared, the sulfur may be removed from the carbon nanopores at temperatures of 150° C. and above. Similar results will be understood to apply also to Se and Te nanocomposites, at a temperature consistent with such other composites. For example, at about 175° C. under vacuum for Se and 400° C. under vacuum for Te. Such a temperature dependency provides for optimization of the sulfur content in the carbon pores, by conducting the insertion at various temperatures, or post-processing the sulfur-carbon nanocomposite at an appropriate temperature. For example, where the sulfur is driven into the pores of the carbon substrate in an aqueous medium using sonication, the loading of the sulfur in the nanocomposite may range from about 20 wt % to about 80 wt %. In some embodiments, the loading of the sulfur in the nanocomposite may range from about 30 wt % to about 60 wt %. By then heating the sulfur-carbon nanocomposite at various temperatures and for various time periods, some of the sulfur may be removed from the carbon substrate to adjust the sulfur loading in the carbon. Long periods of time at the same temperature will remove more sulfur, and higher temperature and higher vacuum will remove move additional sulfur, or remove the sulfur at a faster rate.

In another aspect, a process is provided for preparing a $Li_2S$ carbon nanocomposite. Alternative to the sonication of aqueous mixtures of an E containing salt with a carbon substrate, insertion of $LiS_2$ into a porous carbon substrate may be conducted in the solid state. For example, $Li_2S$ may be inserted in a porous carbon substrate using sonication at elevated temperatures. Thus, the process includes heating a lithium-sulfur salt in the presence of the porous carbon substrate. The process may include heating a salt that includes lithium and sulfur to a to a temperature from about 500° C. to about 1000° C. In some embodiments, the temperature is from about 700° C. to about 900° C. In one embodiment, the temperature is about 850° C. The lithium-sulfur salt may include any lithium salt that includes sulfur in the anion. For example, the lithium-sulfur salt may include, but is not limited to, salts such as $Li_2SO_4$ and $Li_2SO_3$, and hydrates thereof.

For example, according to one embodiment, the process may be summarized as:

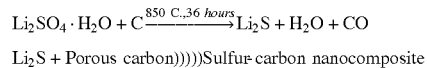

$Li_2S$ + Porous carbon)))))Sulfur-carbon nanocomposite

In the process it is noted that where the lithium salt is hydrated $Li_2SO_4$, the water is removed at about 130° C., and the $Li_2SO_4$ begins reducing to $Li_2S$ at about 500° C. Although the kinetics of this particular reaction are slow at this temperature, the kinetics increase with increasing temperature. At 850° C., complete conversion of the $Li_2SO_4$ to $Li_2S$ takes about 36 hours.

In some embodiments, the contacting and/or the sonicating is performed under an inert atmosphere or in a reducing atmosphere. The high temperatures of the reaction to generate lithium metal and elemental sulfur may result in oxidation of such products if the reaction is conducted in the presence of oxygen or oxidizing agents. Accordingly, the processes may be protected from air and other oxidizing agents. Illustrative inert gases that may be used include, nitrogen, helium, neon, and argon. Illustrative reducing atmospheres include, but are not limited to those which contain hydrogen. The reducing atmosphere may also include a mixture of hydrogen with an inert gas. In one embodiment, the amount of hydrogen in the gas may be from about 0.1 vol % to about 5 vol %.

The porous carbon substrate into which the $Li_2S$ is inserted, may include high surface area carbon materials and/or nanoparticulate carbon materials. Such materials may include, but are not limited to, microporous carbon, mesoporous carbon, mesoporous microbeads, graphite, expandable graphite, graphene, carbon black, or carbon nanotubes. Commercial examples of carbon black include, but are not limited to, Super P, Black Pearl 2000, Denka Black, Vulcan XC72R, Ketjen black.

The sonicating of the aqueous mixture may be conducted at a frequency sufficient to drive the $Li_2S$ into the pores of the porous carbon substrate. For example, the sonicating may be performed at a frequency from about 20 Hz to about 100 Hz.

The amount of $Li_2S$ that is driven into the pores of the carbon substrate may range from about 20 wt % to about 80 wt %. In some embodiments, the amount of $Li_2S$ in the carbon substrate may range from about 30 wt % to about 60 wt %.

The nanocomposites thus prepared may be employed in the preparation of an electrochemical cell. Such an electrochemical cell includes a cathode, an anode, a separator, and an electrolyte. It is the cathode that includes either a S-carbon nanocomposite, a Se-carbon nanocomposite, a Te-carbon nanocomposite, or a lithium sulfur carbon nanocomposite. The nanocomposites may be prepared in a slurry with a binder and applied to a current collector for formation of the cathode.

To form the slurry of the nanocomposite with the binder, the binder is dissolved in a solvent and slurried with the nanocomposite, prior to application to the current collector and solvent removal. Suitable solvents include, but are not limited to, water, N-methylpyrrolidone (NMP), acetone, toluene, dimethylformamide (DMF), and dimethylsulfoxide (DMSO), as well as mixtures of any two or more such solvents.

The current collector provides contact between the electroactive material and an external load to allow for the flow of electrons through a circuit to which the electrode is connected. The current collector may be a conductive material. Illustrative current collectors include, but are not limited to, aluminum, nickel, platinum, palladium, gold, silver, copper, iron, stainless steel, rhodium, manganese, vanadium, titanium, tungsten, or aluminum carbon coated or any carbon-coated metal described above.

Illustrative binders include, but are not limited to, polyvinylidene difluoride (PVDF), polyvinyl alcohol (PVA), polyethylene, polystyrene, polyethylene oxide, polytetrafluoroethylene (Teflon), polyacrylonitrile, polyimide, styrene butadiene rubber (SBR), carboxy methyl cellulose (CMC), alginate, gelatine, a copolymer of any two or more such polymers, or a blend of any two or more such polymers. In one embodiment, the binder is alginate.

The electrodes may also contain a wide variety of other additives that are known in the art for use in electrodes. Illustrative additives include, but are not limited to, manganese dioxide, iodine, silver chromate, silver oxide and vanadium pentoxide, copper oxide, copper oxyphosphate, lead sulfide, copper sulfide, iron sulfide, lead bismuthate, bismuth trioxide, cobalt dioxide, or copper chloride.

The electrodes may also contain a conductive polymer. Illustrative conductive polymers include, but are not limited to, polyaniline, polypyrrole, poly(pyrrole-co-aniline), polyphenylene, polythiophene, polyacetylene, or polysiloxane.

Anodes of the electrochemical cell may include lithium metal, lithiated silicon, lithiated tin, or lithiated graphite.

The separator of the electrochemical may be a polymer or ceramic separator. For example, the separate may include, but is not limited to, polypropylene (PP), polyethylene (PE), trilayer (PP/PE/PP), or polymer films coated with alumina based ceramic particles.

As noted above, the electrochemical cell also includes an electrolyte. Suitable electrolytes include a solvent and a salt. The salt may include alkali metal salts in general, and lithium metal salts in some specific embodiments. Suitable salts include those such as, but not limited to, $LiPF_6$, $LiClO_4$, $Li[B(C_2O_4)_2]$, $Li[BC_2O_4F_2]$, $Li[PF_4(C_2O_4)]$, $Li[PF_2(C_2O_4)_2]$, $Li[N(CF_3SO_2)_2]$, $Li[C(SO_2CF_3)_3]$, $Li[N(C_2F_5SO_2)_2]$, $LiCF_3SO_3$, $Li_2B_{12}X_{12-n}H_n$, $Li_2B_{10}X_{10-n'}H_{n'}$, where X is a halogen, n is an integer from 0 to 12, and n' is an integer from 0 to 10, $LiNO_3$, LiCl, LiBr, LiF, $LiAlF_4$, $LiBF_4$, $Li(FSO_2)_2N$, $Li_2SO_4$, $LiAlO_2$ LiSCN, LiI, $LiAsF_6$, $LiB(Ph)_4$, $LiSO_3CH_3$, $Li_2S_{x''}$, $Li_2Se_{x''}$, $(LiS_{x''}R)_y$, or $(LiSe_{x''}R)_y$; wherein x'' is an integer from 1 to 20, y is an integer from 1 to 3 and R is H, alkyl, alkenyl, aryl, ether, F, $CF_3$, $COCF_3$, $SO_2CF_3$, or $SO_2F$. The salt may be present in the electrolyte from about 0.05 wt % to about 40 wt %.

Alkali metal salts such as $LiPF_6$, $LiClO_4$, $Li[B(C_2O_4)_2]$, $Li[BC_2O_4F_2]$, $Li[PF_4(C_2O_4)]$, $Li[PF_2(C_2O_4)_2]$, $Li[N(CF_3SO_2)_2]$, $Li[C(SO_2CF_3)_3]$, $Li[N(C_2F_5SO_2)_2]$, $LiCF_3SO_3$, $Li_2B_{12}X_{12-n}H_n$, $Li_2B_{10}X_{10-n'}H_{n'}$, where X is a halogen, n is an integer from 0 to 12, and n' is an integer from 0 to 10, $LiNO_3$, LiCl, LiBr, LiF, $LiAlF_4$, $LiBF_4$, $Li(FSO_2)_2N$, $Li_2SO_4$, $LiAlO_2$ LiSCN, LiI, $LiAsF_6$, $LiB(Ph)_4$, and $LiSO_3CH_3$, may also be used in a dual role as an electrode stabilizing additive, in some embodiments. Where the electrolyte includes a salt used as an electrode stabilizing additive, the salt may be present in the electrolyte from about 0.05 wt % to about 20 wt %.

The solvent for use in the electrolyte may include a fluorinated ether solvent, cyclic ether solvent, a siloxyl ether solvent, a silyl carbonate solvent, a siloxyl carbonate solvent, a sulfone solvent, or a lactone solvent. In some embodiments, the solvent is a mixture of a fluorinated and a cyclic ether. For example, the solvent may be a mixture of a fluorinated solvent and 1,3-dioxolane, or a fluorinated solvent and tetrahydrofuran, or a fluorinated solvent and a pyran, or a fluorinated solvent and a dioxane. The solvent or mixture of solvents may include sulfones such as ethyl methyl sulfone, tetramethyl sulfone, butyl sulfone, 1-fluoro-2-methyl-sulfonylbenzene, ethyl vinyl sulfone, dimethyl sulfone, or γ-butyrolactone.

Where the solvent includes a fluorinated ether solvent, it may be represented by Formula I or II.

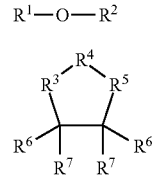

Formula I

Formula II

In Formulas I and II, each $R^1$ and $R^2$ is individually a $C_nH_xF_y$ group; $R^3$ and $R^5$ are individually O or $CR^6R^7$; $R^4$ is O or C=O; each $R^6$ and $R^7$ is individually H, F or a $C_nH_xF_y$ group; n is 1 to 20; x is 0 to 2n; and y is 1 to 2n+1. However, the Formulas are subject to the proviso that at least one $R^6$ or $R^7$ is other than H, and $R^4$ is not O when $R^3$ or $R^5$ is O.

It has been observed that the presence of a fluorinated ether-based electrolyte can significantly improve the cycle performance and columbic efficiency of the cell. For example, when 1M LiTFSI in a mixture of 1,3-dioxlane and dimethoxyethane was used as electrolyte, the cell delivers 932 mAh/g in the first cycle and 409 mAh/g capacity in the $100^{th}$ cycle with a capacity retention of 44%. The average coulombic efficiency during cycling is only around 60%. When 1M LiTFSI in a mixture of 1,3-dioxlane and 1,1,2,2-tetrafluoro-3-(1,1,2,2-tetrafluoroethoxy)propane (D2) was used as electrolyte, better cycling performance can be achieved, the coulombic efficiency is always higher than 96%.

Where the fluorinated ether solvent is represented by Formula I, $R^1$ and $R^2$ may be individually $CF_2CF_3$; $CH_3$; $CH_2CH_3$, $CF_2CHF_2$; $CF_2CH_2F$; $CF_2CH_3$; $CF_2CF_2CF_3$; $CH_2CF_2CHF_2$; $CF_2CF_2CHF_2$; $CF_2CF_2CH_2F$; $CF_2CF_2CH_3$; $CF_2CF_2CF_2CF_3$; $CF_2CF_2CF_2CH_3$; $CF_2CF_2CF_2CF_2CF_3$; $CF_2CF_2CF_2CF_2CHF_2$; $CF_2CF_2CF_2CF_2CH_2F$; $CF_2CF_2CF_2CF_2CH_3$; $CF_2CF_2OCF_3$; $C_2F_5CF(CF(CF_3)_2)$, provided that $R^1$ or $R^2$ are both at least partially fluorinated. Illustrative fluorinated ether solvents include, but are not limited to, $CHF_2CF_2OCF_2CF_2CF_2H$; $CF_3CF_2OCF_2CF_3$; $CF_3CF_2CF_2OCF_2CF_2CF_3$; $CHF_2CF_2CH_2OCF_2CH_3$, $CHF_2CF_2CH_2OCF_2CF_3H$, $CHF_2CF_2CH_2OCF_2CH_3$, $CF_3CF_2CF_2OCF_2CF_2CF_3$; $CF_3OCF_2CF_2OCF_2CF_2CF_3$; $CF_3CF_2OCF_2CH_2F$;

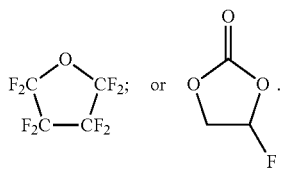

In some embodiments, the electrolyte includes a silyl ether solvent, a silyl carbonate, or a siloxyl carbonate. For example, the electrolyte may include a compound of Formula $(R^8)_3SiOR^9R^{10}$. In the formula, each $R^8$ is independently alkyl or alkoxyl; $R^9$ is alkylene, alkyleneoxy, or polyalkyeneoxy; and $R^{10}$ is alkyl, alkoxy, or cyclic carbonate. In some embodiments, the electrolyte may include a compound represented as $Si(CH_3)_3(OCH_2CH_2)_{n'}OCH_3$, or $Si(CH_3)_3(OCH_2CH_2)_{n'}OR^{11}$, n' is from 1 to 8, and $R^{11}$ is a group of Formula

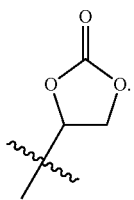 [SMILES: *C1COC(=O)O1]

The electrolytes described above exhibit excellent coulombic efficiency of greater than about 99%, compared to conventional non-fluorinated electrolytes which exhibit a coulombic efficiency of from about 60 to 70%.

The present invention, thus generally described, will be understood more readily by reference to the following examples, which are provided by way of illustration and are not intended to be limiting of the present invention.

EXAMPLES

Example 1

Preparation of $Li_2S$. Mesoporous carbon (3 g; Sigma-Aldrich) was mixed with $Li_2SO_4 \cdot H_2O$ (2 g) in the solid state. The mixture was then heated to 850° C. under argon for 36 hours. After heating, the combined weight loss due to CO generation and dehydration was about 2 g. The $Li_2S$-carbon ($Li_2S$—C) nanocomposite was shown by x-ray diffraction to be a pure phase. See FIG. 1. The x-ray diffraction (XRD) pattern of the $Li_2S$—C nanocomposite shows a face-centered cubic crystalline material with carbon in a pure phase.

Example 2

Figure 2:
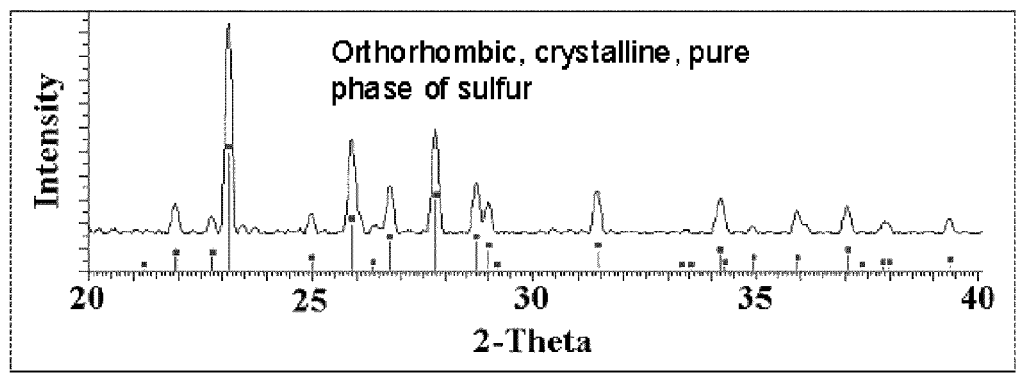
FIG. 2 is an XRD spectrum of a S-carbon nanocomposite prepared according to Example 2.

Preparation of S—C Nanocomposites. Mesoporous carbon (0.5 g; Sigma-Aldrich, 10 nm pores) was suspended in water (50 ml). To the suspension was added, with stirring, $Na_2S_2O_3$ (4.9 g in 5 ml of water), and HCl (5 ml diluted with 10 ml water) to adjust the pH to about 4. The resulting suspension/solution was then sonicated using a VCX 500 Sonifier operating at 20 kHz for 0.5 hours, in a sound abating enclosure. After sonication, the sulfur-mesoporous carbon nanocomposite (S—C nanocomposite) was recovered by filtration and dried in a 110° C. oven. The XRD pattern of the material is shown in FIG. 2. The figure illustrates that the sulfur is an orthorhombic, crystalline pure solid. Using the above amounts of carbon, $Na_2S_2O_3$, and HCl, a loading density of about 34% was achieved of S in carbon. Higher loading densities (i.e. grams S per grams carbon) may be achieved.

Figure 3:
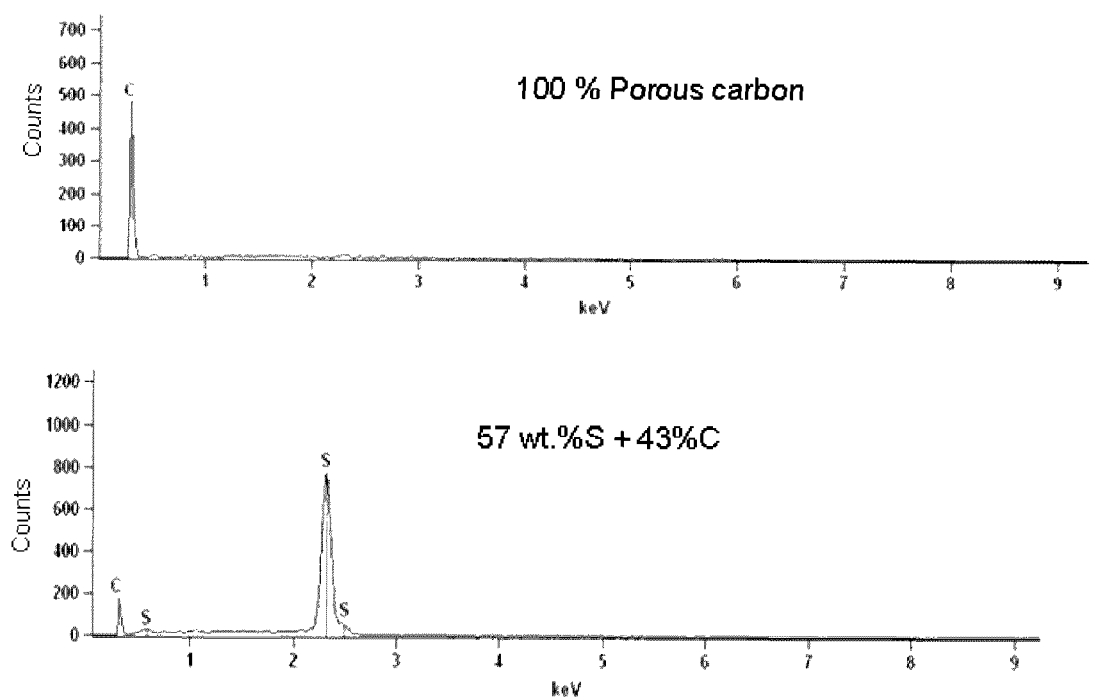
FIGS. 3A and 3B is an energy dispersive x-ray (EDAX) spectrum of a porous carbon substrate before (3A) and after (3B) sulfur insertion according to Example 2.

Energy dispersive x-ray analysis (EDAX) shows the insertion of the sulfur into the pores of the mesoporous carbon (FIGS. 3A and B). In FIG. 3A, the carbon prior to sulfur insertion is shown and FIG. 3B is after insertion. The local environment was also tested by targeting different points throughout the sample. Nearly identical EDAX spectra illustrated that inclusion of the sulfur is nearly homogeneous throughout the carbon.

Testing of the S—C nanocomposite material showed that at or above 150° C., the sulfur sublimes out from the carbon pores of the mesoporous carbon.

Example 3

Cyclic Voltammetry Results of Various Li/Electrolyte/S—C Nanocomposites. Sulfur-carbon nanocomposites prepare as in Example 2, above, were subjected to cyclic voltammetry (CV) under a variety of conditions. The electrolytes are shown in Table 1.

TABLE 1

Electrolyte Compositions And Peak Data

| | Electrolyte Components | | | |
|---|---|---|---|---|
| Sample | Electrolyte Solvent (ratio, for mixtures, vol/vol) | Electrolyte Salt | Cathodic Peaks | Anodic Peaks |
| A | DOL/DME (1:2) | 1M LiTFSI | 2.36, 2.05 | 2.35, 2.4 |
| B | DOL/TEGDME (1:2) | 1M LiTFSI | 2.45, 1.98 | 2.40, 2.50 |
| C | DOL/TEGDME (1:2) | 1M LiOTf | 2.43, 2.07 | 2.11, 2.24, 2.46 |
| D | DOL/D2 (1:2) | 1M LiTFSI | 2.22, 1.73 | 2.47 |
| E | DOL/D2 (1:2) | 1M LiOTf | 2.40(s), 2.02 | 2.37, 2.45 |

DME is dimethoxyethane ($H_3COCH_2CH_2OCH_3$);
TEGDME is tetraethyleneglycoldimethoxyethane ($H_3C(OCH_2CH_2)_4OCH_3$) DOL is dioxolane;
LiTFSI is lithium bis-(trifluoromethyl)sulfonamide;
LiOTf is lithium trifluoromethane sulfonate; and
D2 is $CHF_2CF_2CH_2OCF_2CF_2H$.

The cathodic and anodic peaks are the result illustrated by the following reaction sequence:

In the reaction, the $S_8$ is converted to lithium polysulfides species at a discharge plateau of about 2.2 V to about 2.4 volts. The lithium polysulfide is converted to $Li_2S_2$ or $Li_2S$ at a voltage of from about 1.7 V to about 2.0V.

Figure 4:
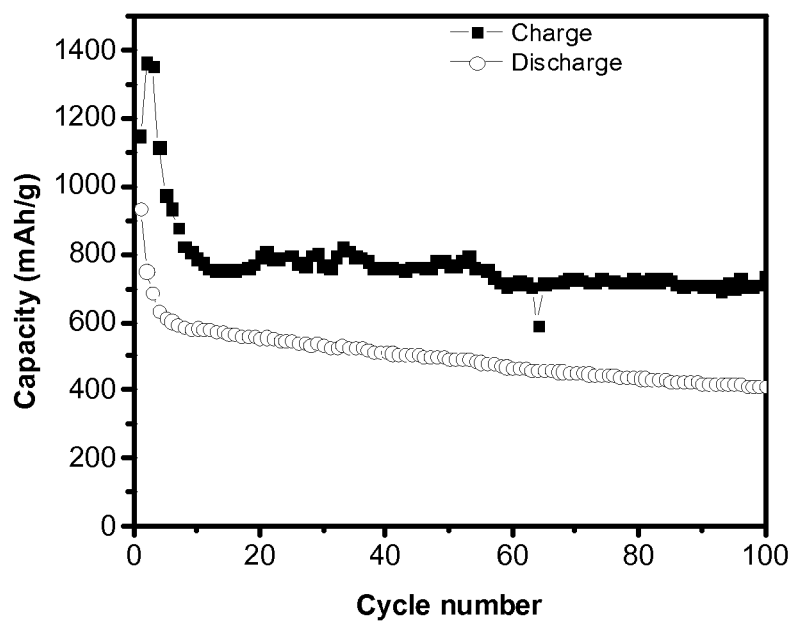
FIG. 4 is a capacity v. cycle number profile for a S-carbon nanocomposite in conjunction with a dioxolane and dimethoxyethane based electrolyte, described as Sample A in Table 1 of the examples.
Figure 5:
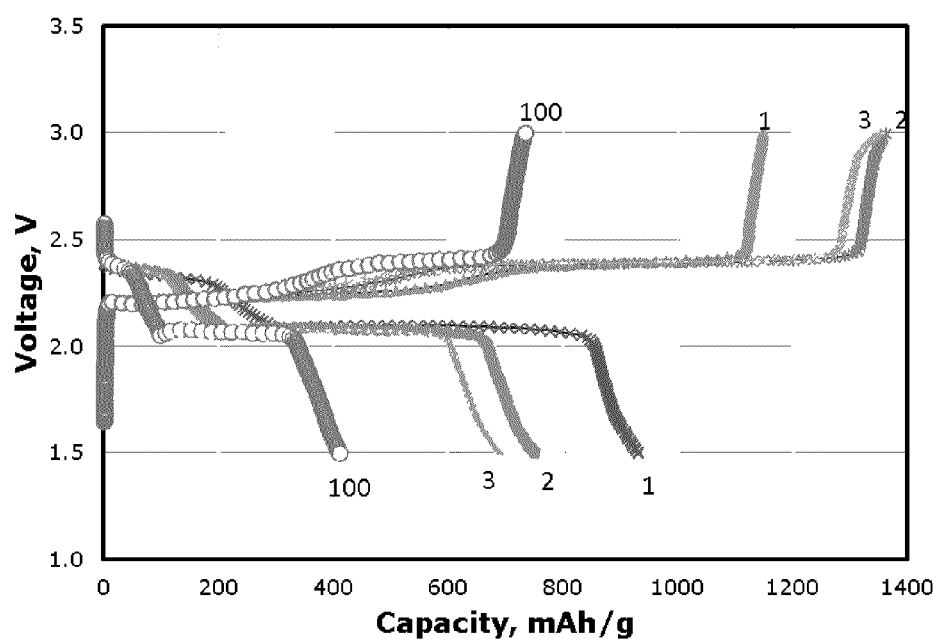
FIG. 5 is a voltage v. capacity profile for a S-carbon nanocomposite in conjunction with a dioxolane and dimethoxyethane based electrolyte, described as Sample A in Table 1 of the examples.
Figure 6:
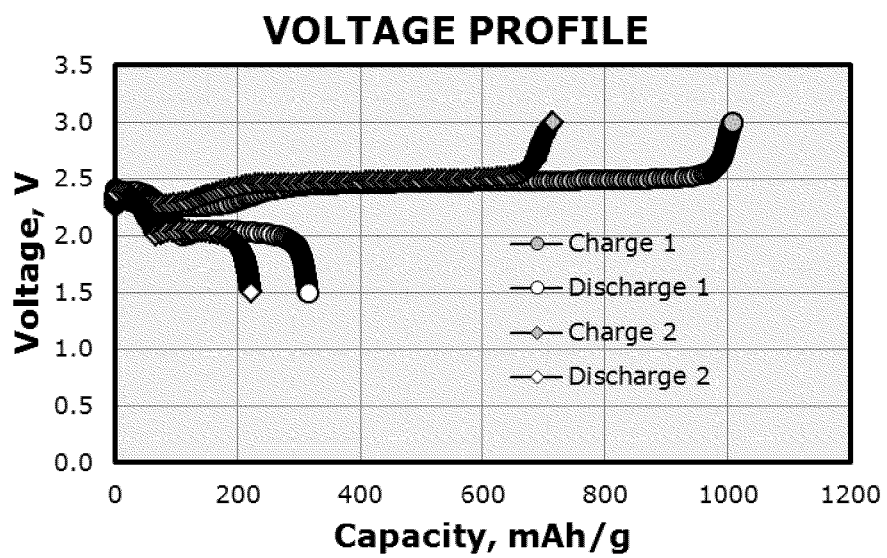
FIG. 6 is a capacity v. cycle number profile for a S-carbon nanocomposite in conjunction with a dioxolane and tetraethyleneglycoldimethoxyethane based electrolyte, described as Sample B in Table 1 of the examples.
Figure 7:
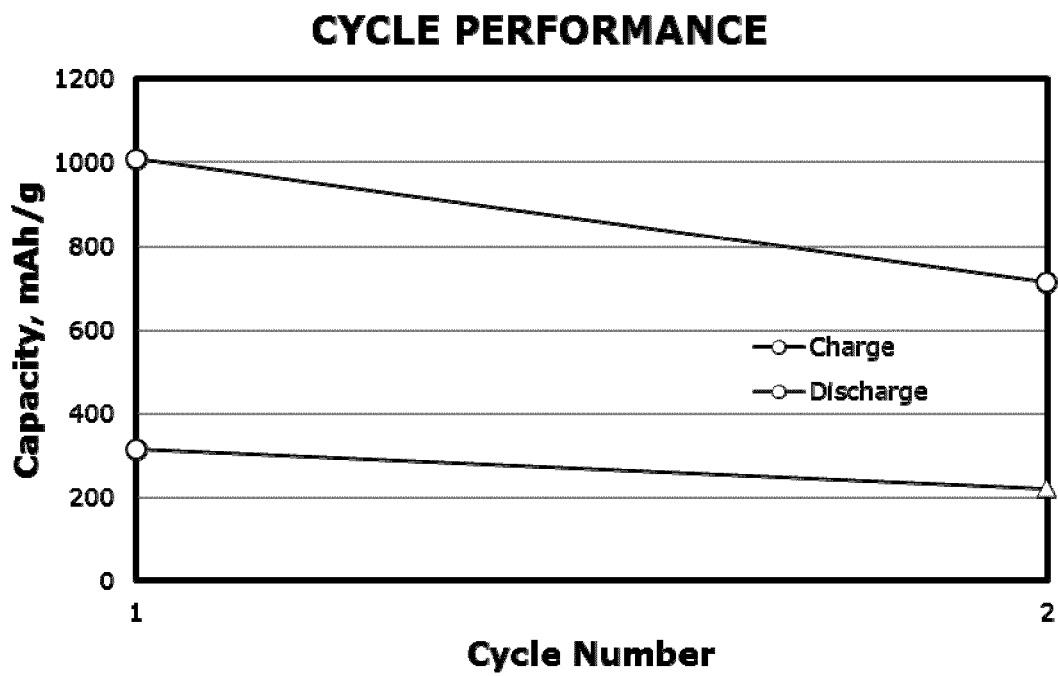
FIG. 7 is a voltage v. capacity profile for a S-carbon nanocomposite in conjunction with a dioxolane and tetraethyleneglycoldimethoxyethane based electrolyte, described as Sample B in Table 1 of the examples.
Figure 8:
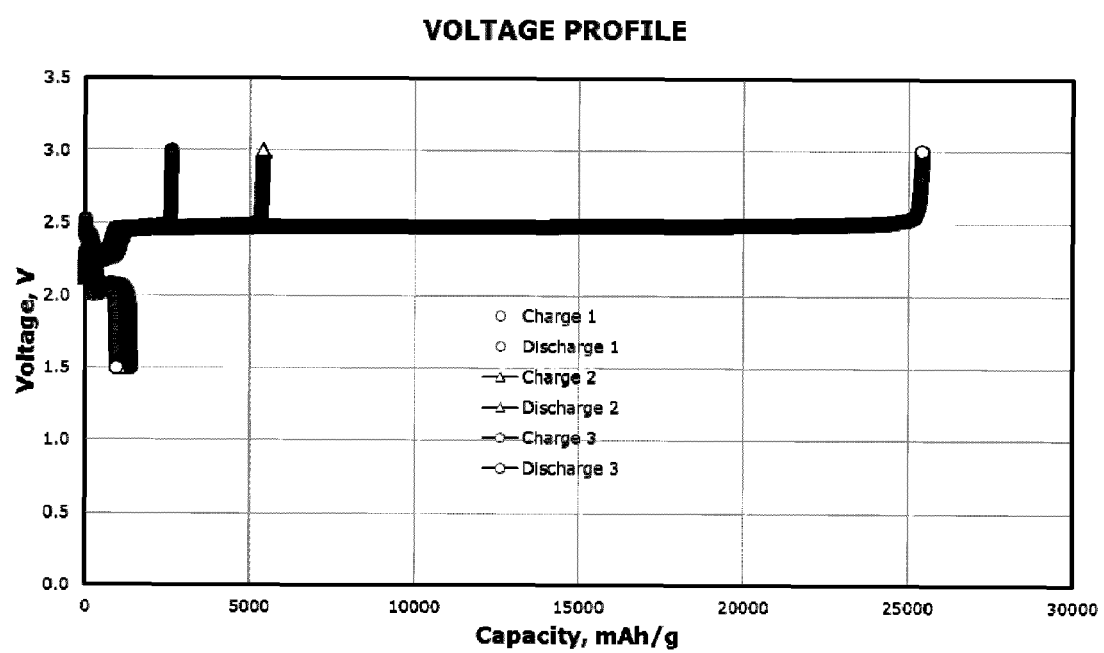
FIG. 8 is a capacity v. cycle number profile for a S-carbon nanocomposite in conjunction with a dioxolane and tetraethyleneglycoldimethoxyethane based electrolyte, described as Sample C in Table 1 of the examples.
Figure 9:
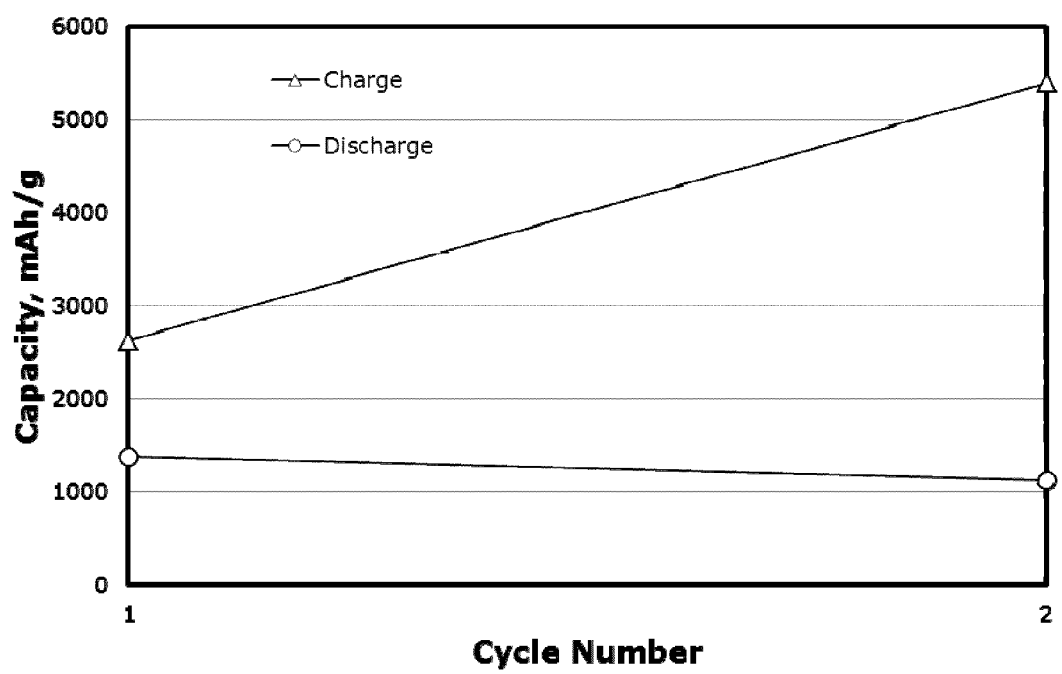
FIG. 9 is a voltage v. capacity profile for a S-carbon nanocomposite in conjunction with a dioxolane and tetraethyleneglycoldimethoxyethane based electrolyte, described as Sample C in Table 1 of the examples.

Observations of the CV results include the following. First, in Sample A (see FIGS. 4 and 5), the discharge potential plateaus occur at about 2.4 V and 2.1 V, and the upper potential plateau decreases upon cycling. The cell showed poor Ah efficiency of about 60%. Sample B (FIGS. 6 and 7) a shuttle effect is observed, causing a low Ah efficiency of about 30%. The discharge capacity of Sample B is also low at less than 400 mAh/g. In Sample C (FIGS. 8 and 9), again, a shuttle effect is observed, causing a low Ah efficiency of about 30%. The discharge capacity of Sample B for the first two cycles was greater than 1000 mAh/g, however the cell did not cycle in the fourth charging.

Figure 10:
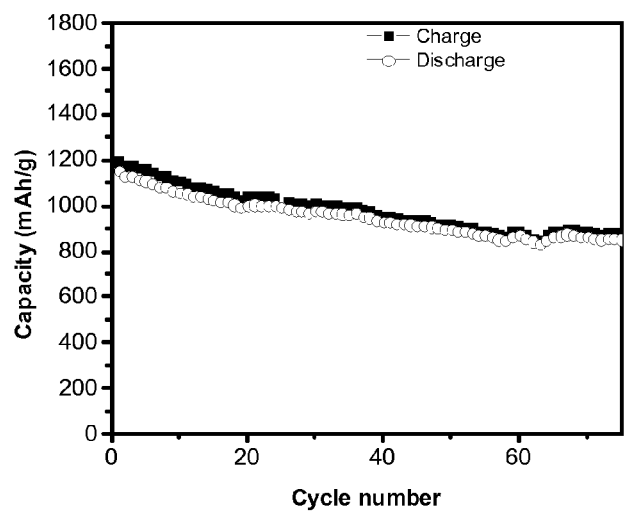
FIG. 10 is a capacity v. cycle number profile for a S-carbon nanocomposite in conjunction with a dioxolane and $CHF_2CF_2CH_2OCF_2CF_2H$ based electrolyte, described as Sample D in Table 1 of the examples.
Figure 11:
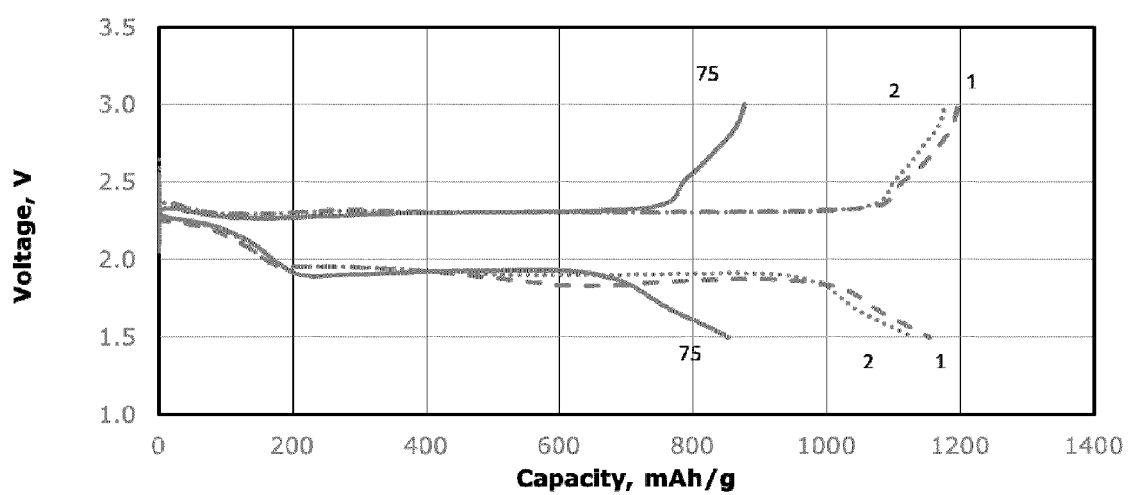
FIG. 11 is a voltage v. capacity profile for a S-carbon nanocomposite in conjunction with a dioxolane and $CHF_2CF_2CH_2OCF_2CF_2H$ based electrolyte, described as Sample D in Table 1 of the examples.

Sample D (FIGS. 10 and 11) showed the best performance. Good Ah efficiency (96-97%) was observed. It is also noteworthy that in this solvent the $Li_2S$ or $Li_2S_2$ is not soluble, and no shuttle behavior was observed. After 75 cycles, Sample D exhibited a discharge capacity of greater than about 800 mAh/g. With Sample D, the first discharge step was stable, and the second was shorter upon cycling. Capacity fading was mostly observed in the second discharge step representing the formation of $Li_2S_2$ from $Li_2S_x$ (4<x<8). Only a single plateau was observed for the Sample D cells.

Figure 12:
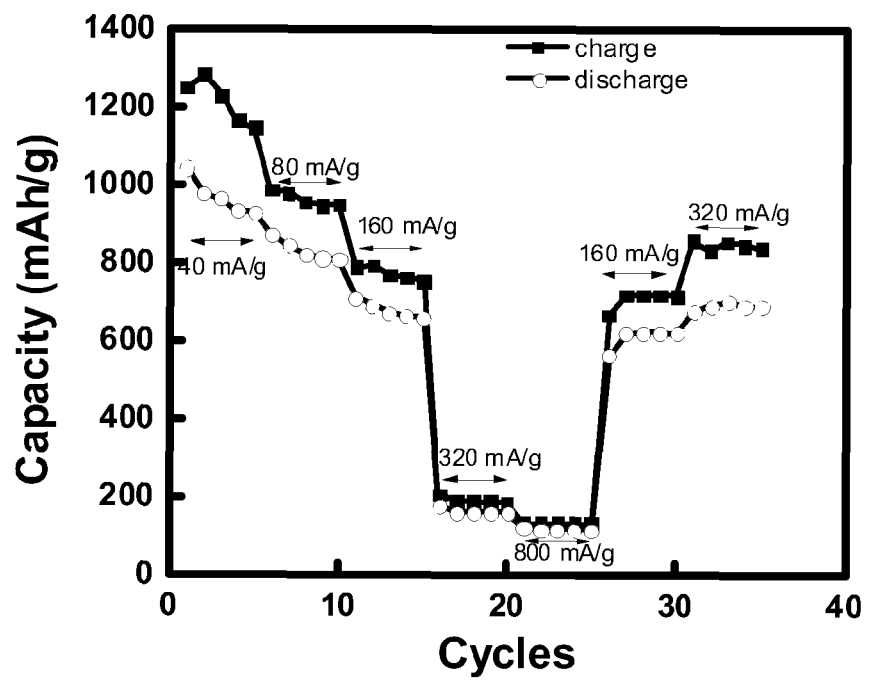
FIG. 12 is a capacity v. cycle profile at various charge/discharge rates for Sample A in Table 1 of the examples.
Figure 13:
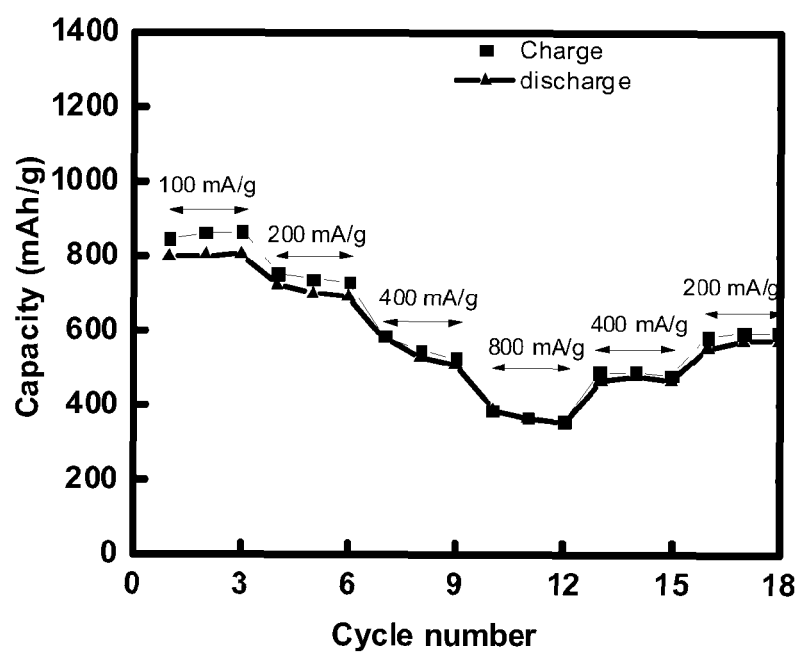
FIG. 13 is a capacity v. cycle profile at various charge/discharge rates for Sample D in Table 1 of the examples.

In FIGS. 12 and 13, the capacity v. cycle data is provided at various charge/discharge rates for Samples A (FIG. 12) and D (FIG. 13) in Table 1. As illustrated in the figures, the use of $CHF_2CF_2CH_2OCF_2CF_2H$ as the solvent improves the rate performance of the electrolyte. The lower the current density, the poorer the columbic efficiency. Even at 800 mA/g high rate, a discharge capacity of 400 mAh/g can still be achieved.

Figure 14:
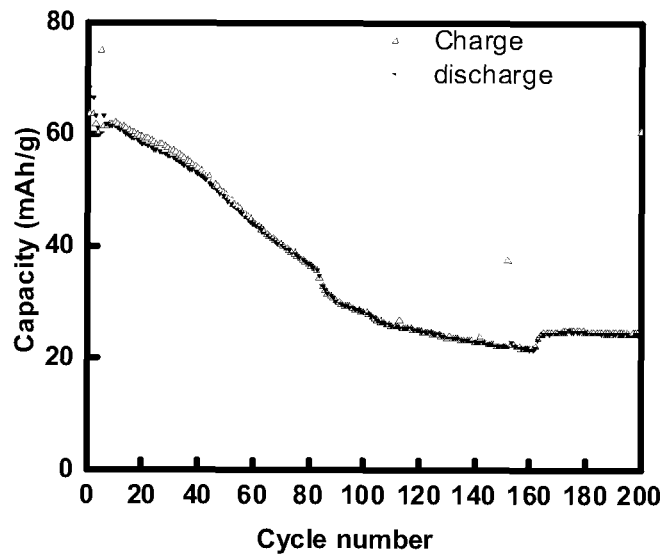
FIG. 14 is a capacity v. cycle profile for a S-carbon nanocomposite with an electrolyte containing 2-[2-[2-[2-methoxy]ethoxy]ethoxy]ethoxy trimethyl silane (1NM3) and $CHF_2CF_2CH_2OCF_2CF_2H$ in a ratio of 1:2 vol/vol with 1M LiTFSI, according to the examples.
Figure 15:
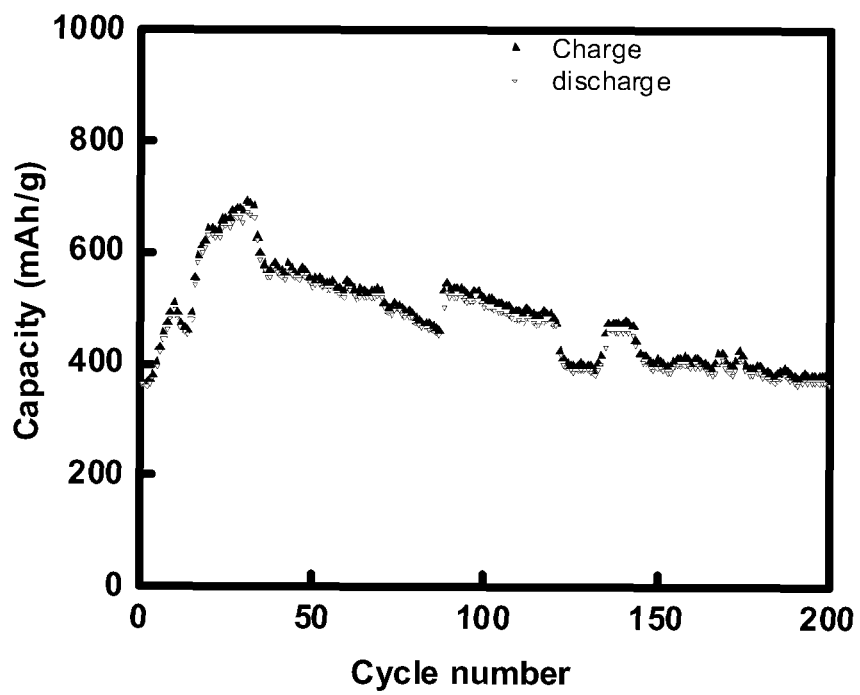
FIG. 15 is a capacity v. cycle profile for a S-carbon nanocomposite with an electrolyte containing dioxolane and $CHF_2CF_2CH_2OCF_2CF_2H$ in a ratio of 1:2 vol/vol with 1M LiTFSI, according to the examples.

Solvent Comparison. A sulfur-carbon nanocomposite material having 48 wt % sulfur and 52 wt % carbon was used and tested in two electrolytes. The first electrolyte contained 2-[2-[2-[2-methoxy]ethoxy]ethoxy]ethoxy trimethyl silane (1NM3) and $CHF_2CF_2CH_2OCF_2CF_2H$ in a ratio of 1:2 vol/vol with 1M LiTFSI. The second electrolyte contained dioxolane and $CHF_2CF_2CH_2OCF_2CF_2H$ in a ratio of 1:2 vol/vol with 1M LiTFSI. Both electrolytes exhibited good Ah efficiency (98%) with low sulfur utilization. FIG. 14 is a capacity v. cycle profile at a current rate of 200 mA/g for a S-carbon nanocomposite with an electrolyte containing 2-[2-[2-[2-methoxy]ethoxy]ethoxy]ethoxy trimethyl silane (1NM3) and $CHF_2CF_2CH_2OCF_2CF_2H$ in a ratio of 1:2 vol/vol with 1M LiTFSI. FIG. 15 is the same cell configuration, but run at a current rate of 100 mA/g.

Figure 16:
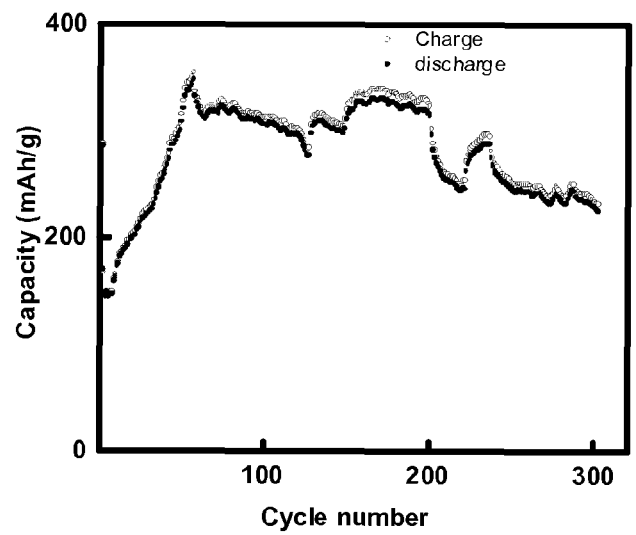
FIG. 16 is a capacity profile for a S-carbon nanocomposite with a sodium alginate binder, according to the examples.
Figure 17:
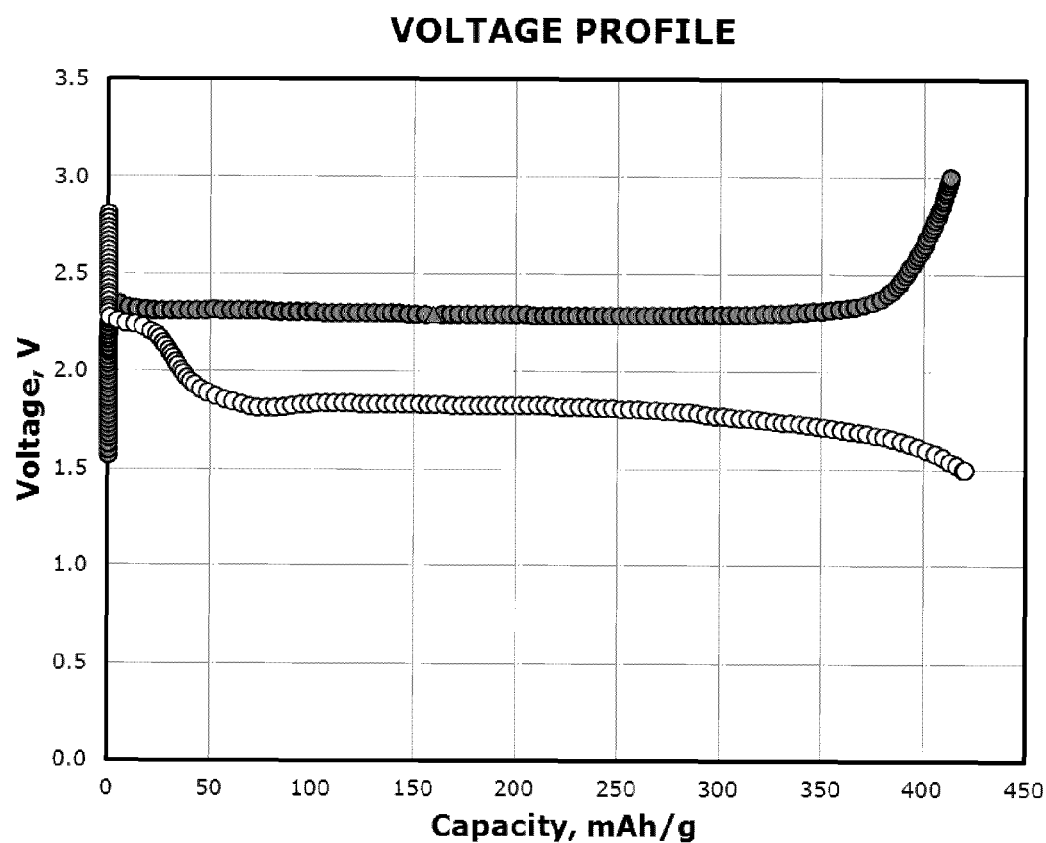
FIG. 17 is a voltage profile for a S-carbon nanocomposite with a sodium alginate binder, according to the examples.

Binder Testing. Electrodes were prepared using sodium alginate as a binder. Sodium alginate is environmentally friendly, water soluble binder. FIGS. 16 and 17 illustrate the capacity and voltage profiles, respectively, for electrodes using sodium alginate binder, with the same sulfur-carbon nanocomposite that was utilized in the solvent comparison of the previous paragraph. About 10 wt % sodium alginate binder (aqueous) was mixed with C—S powder.

Figure 18:
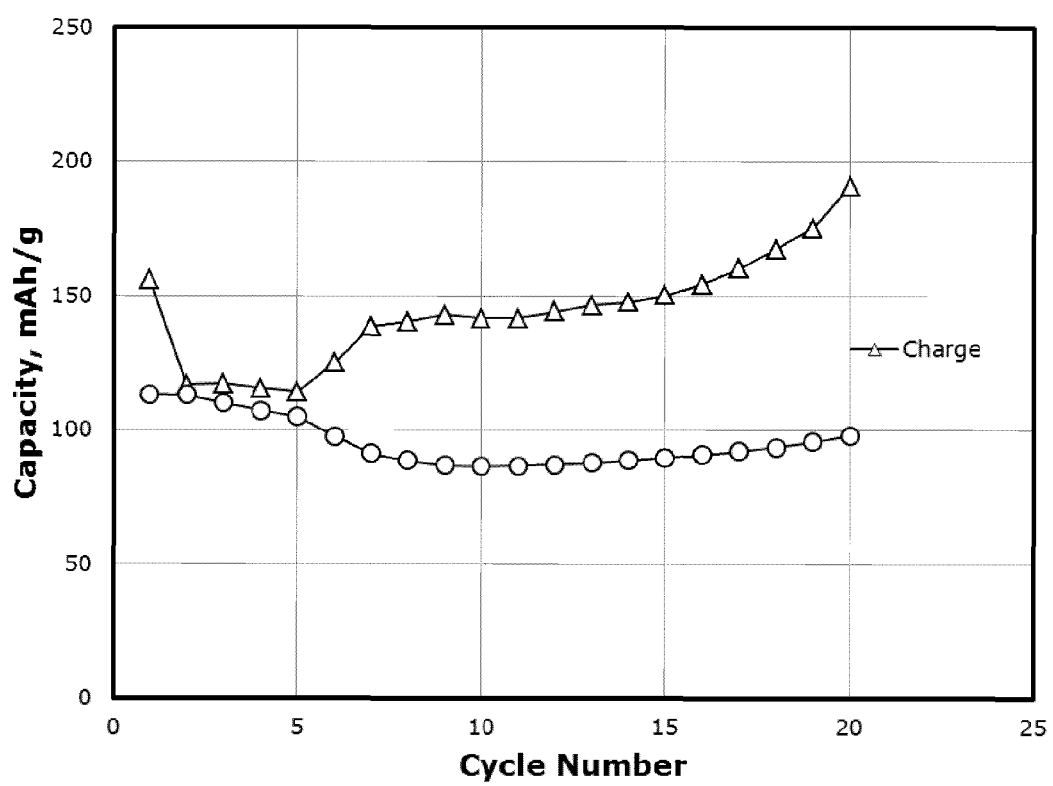
FIG. 18 is a capacity profile for a cell having a S-carbon nanocomposite in an electrolyte containing dioxolane and DME, according to the examples.
Figure 19:
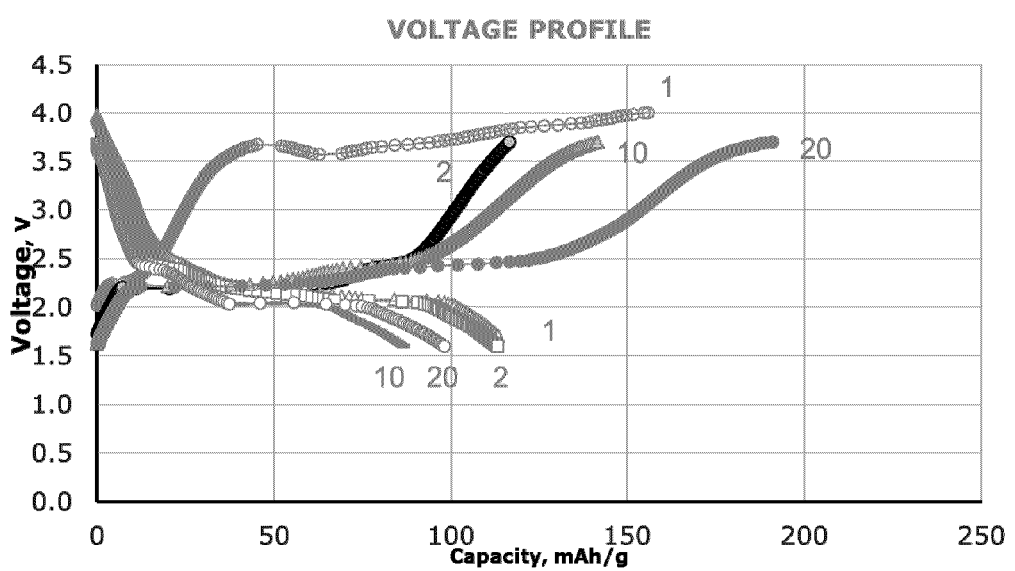
FIG. 19 is a capacity profile for a cell having a S-carbon nanocomposite in an electrolyte containing dioxolane and DME, according to the examples.
Figure 20:
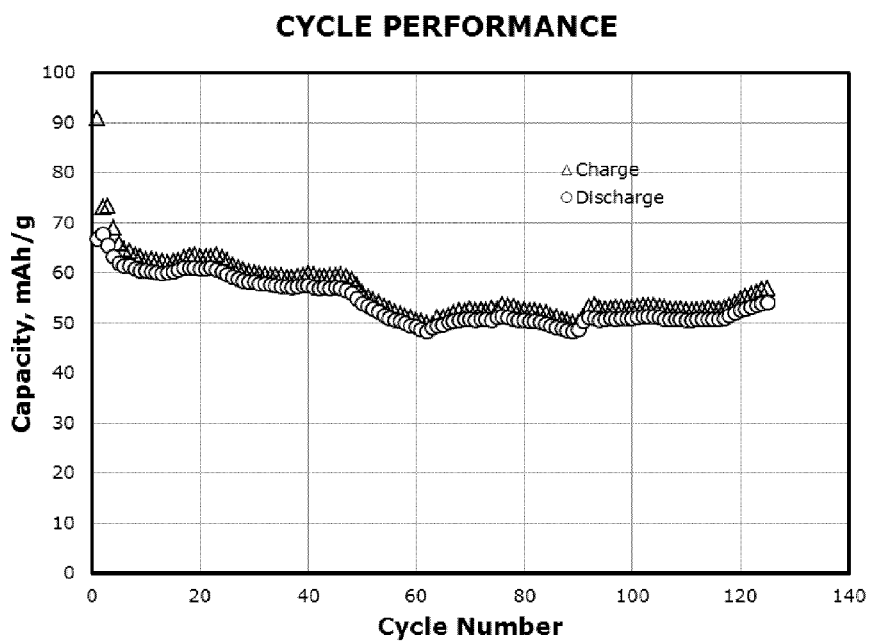
FIG. 20 is a capacity profile for a cell having a S-carbon nanocomposite in an electrolyte containing ethylmethylsulfone, according to the examples.
Figure 21:
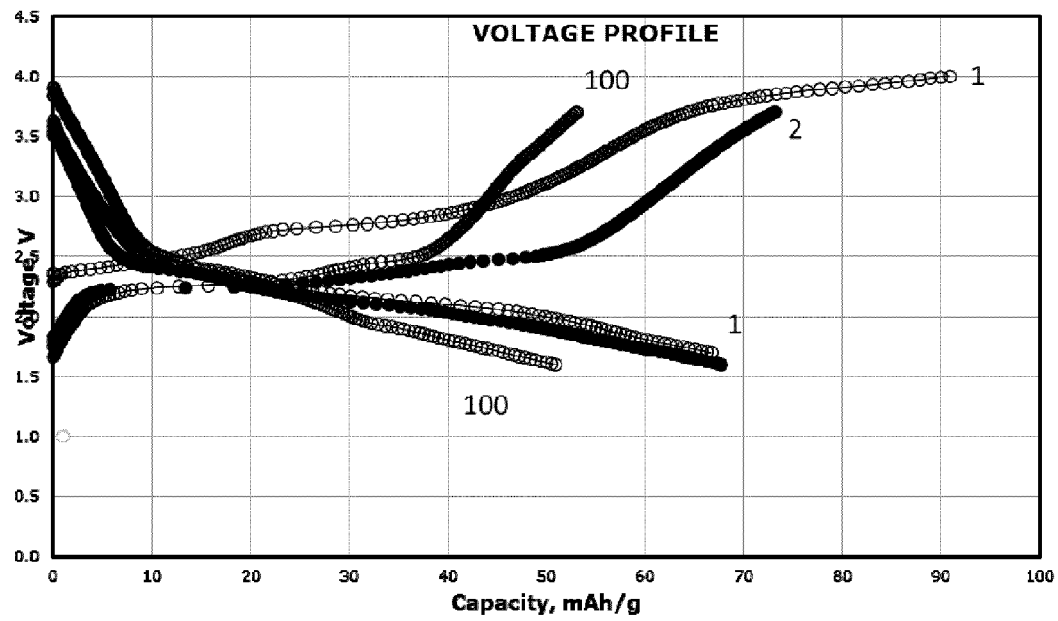
FIG. 21 is a capacity profile for a cell having a S-carbon nanocomposite in an electrolyte containing EMS, according to the examples.

Cycling Performance Testing. The cycling performance of $Li_2S$/Li cells was tested with various electrolytes. The cells were cycled from 4 V to 1.7 V for the first cycle and then from 3.7 V to 1.7 V for the remaining cycles. In one cell, an electrolyte of dioxolane and DME (1:2) was used with 1 M LiTFSI (see FIGS. 18 and 19). The other cell included an electrolyte of EMS with 1 M $LiPF_6$ (see FIGS. 20 and 21). The first cell exhibited a low efficiency, and the charge capacity continually increased upon cycling due to a shut-tling mechanism. The first charge plateau was observed at about 3.5V, however this plateau was not present in subsequent cycles, indicating that the discharge product was not $Li_2S$. In contrast, in the EMS cell, better efficiency was observed, and the shuttle mechanism was not pronounced. However, the cell exhibited low capacity and the charging of the $Li_2S$ was not efficiently active, due to the larger size.

Example 4

Figure 22:
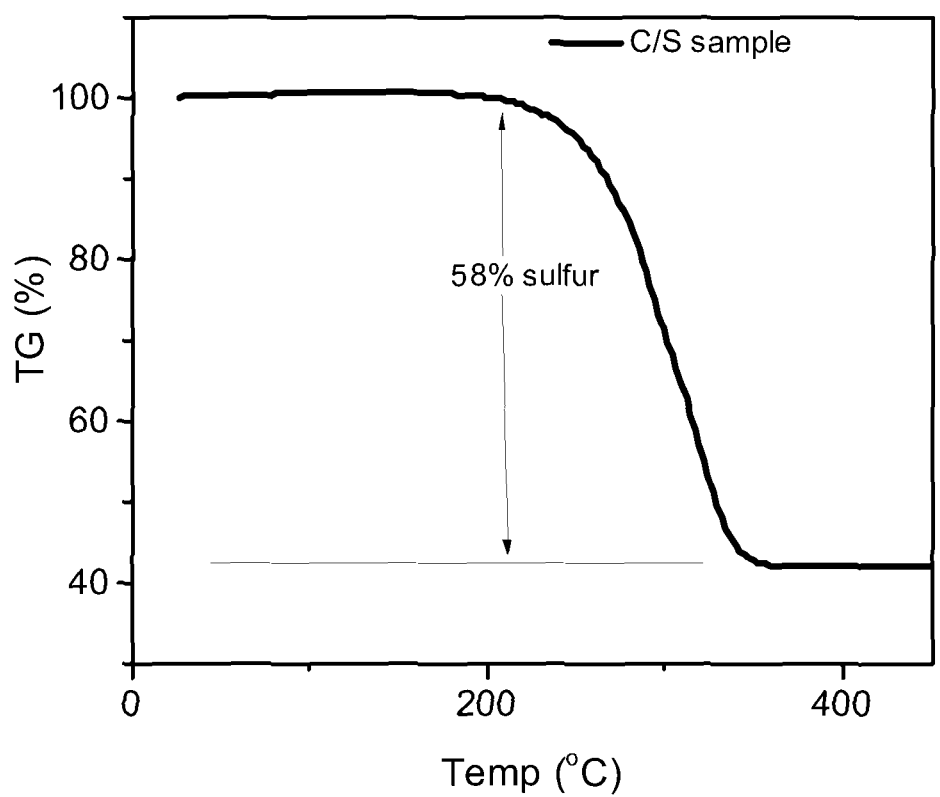
FIG. 22 is a thermogravimetric analysis graph of a S-carbon nanocomposite with 50 wt % sulfur in the carbon, under an Ar atmosphere, according to the examples.

Using the method of Example 2, higher sulfur loading densities in the carbon may be achieved. For example, in FIG. 22, a differential scanning calorimetry (DSC) graph is shown for a S/C sample having approximately 58% sulfur loading in the carbon. In the DSC graph, the sulfur was removed from the carbon, starting at a temperature of about 200° C. The loading densities may range from about 20 wt % to about 80 wt %. In some embodiments, the loading density is from about 30 wt % to about 60 wt %.

Figure 23:
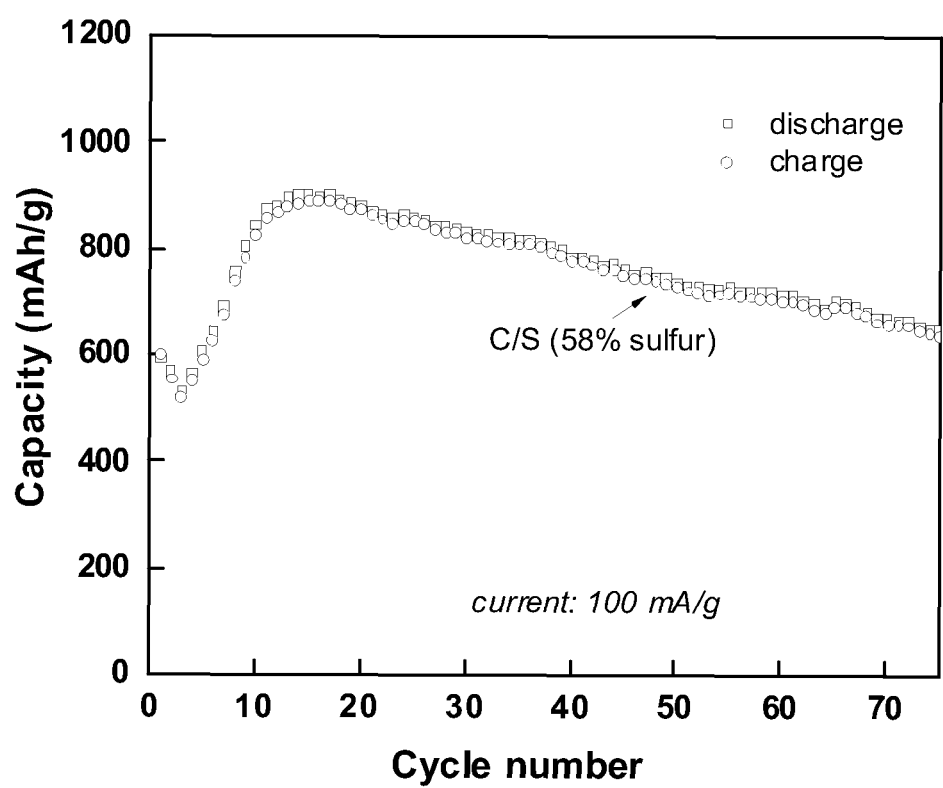
FIG. 23 is a capacity vs. cycle number profile for a S-nanocomposite (58 wt % S) with an electrolyte containing dioxolane and $CHF_2CF_2CH_2OCF_2CF_2H$ in a ratio of 1:2 vol/vol with 1M LiTFSI, according to the examples.

FIG. 23 is a capacity vs. cycle number profile for the 58 wt % S-carbon nanocomposite with an electrolyte containing dioxolane and $CHF_2CF_2CH_2OCF_2CF_2H$ in a ratio of 1:2 vol/vol with 1M LiTFSI examples. The current density in FIG. 23 is 100 mA/g. FIG. 23 indicates that the capacity retention of the sample is approximately 650 mAh/g, even after 70 cycles, where the cell was cycled with 100 mAh/g. The cells require initial break-in cycle period to achieve the maximum discharge capacity. This may be due to incomplete wetting or the presence of large sulfur particles in the initial cycles.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A process of preparing an E-carbon nanocomposite, the process comprising:
   contacting a porous carbon substrate with an E-containing material to form a mixture; and
   sonicating the mixture to form the E-carbon nanocomposite;
   wherein:
      E is S, Se, or Te;
   and wherein the step of sonicating produces elemental E.

2. The process of claim 1, wherein the E-containing material is a salt.

3. The process of claim 2, wherein the salt and the porous carbon substrate are contacted in an aqueous medium.

4. The process of claim 3, wherein the aqueous medium further comprises an acid.

5. The process of claim 1, wherein E-containing material comprises $Na_2S_2O_3$, $Li_2S_2O_3$, $K_2S_2O_3$, $(NH_4)_2S_2O_3$, or a hydrated form of $Na_2S_2O_3$, $Li_2S_2O_3$, $K_2S_2O_3$, or $(NH_4)_2S_2O_3$.

6. The process of claim 1, wherein the S, Se, or Te in the E-carbon nanocomposite is present from about 30 wt % to about 60 wt %.

7. The process of claim 1, wherein the porous carbon substrate comprises microporous carbon, mesoporous carbon, mesoporous microbeads, graphite, expandable graphite, graphene, carbon black, or carbon nanotubes.

8. A process of preparing a $Li_2S$-carbon nanocomposite, the process comprising:
   contacting a porous carbon substrate with a material containing lithium and sulfur in a solid state to form a mixture;
   heating the mixture to form a heated mixture at a temperature; and
   sonicating the heated mixture to form the $Li_2S$-carbon nanocomposite.

9. The process of claim 8, wherein the contacting and sonicating are performed under an inert atmosphere, or in a reducing atmosphere comprising an inert gas and hydrogen.

10. The process of claim 8, wherein the temperature is from about 600° C. to about 1000° C.

11. The process of claim 8, wherein the $Li_2S$-carbon nanocomposite has from 20 wt % to 80 wt % sulfur.

12. The process of claim 8, wherein the porous carbon substrate comprises microporous carbon, mesoporous carbon, mesoporous microbeads, graphite, expandable graphite, graphene, carbon black, or carbon nanotubes.

* * * * *